(12) United States Patent
Fung et al.

(10) Patent No.: US 11,497,639 B2
(45) Date of Patent: Nov. 15, 2022

(54) ENDOVASCULAR PROSTHESIS DELIVERY DEVICE

(71) Applicant: Evasc Neurovascular Enterprises ULC, Vancouver (CA)

(72) Inventors: Eric Soun-Sang Fung, Vancouver (CA); Jonathan G. Tippett, Vancouver (CA)

(73) Assignee: Evase Neurovascular Enterprises ULC

( * ) Notice: Subject to any disclaimer, the term of this patent is extended or adjusted under 35 U.S.C. 154(b) by 386 days.

(21) Appl. No.: 16/338,188

(22) PCT Filed: Sep. 29, 2017

(86) PCT No.: PCT/CA2017/051163
§ 371 (c)(1),
(2) Date: Mar. 29, 2019

(87) PCT Pub. No.: WO2018/058254
PCT Pub. Date: Apr. 5, 2018

(65) Prior Publication Data
US 2020/0022830 A1    Jan. 23, 2020

Related U.S. Application Data

(60) Provisional application No. 62/495,961, filed on Sep. 30, 2016.

(51) Int. Cl.
*A61F 2/966* (2013.01)
*A61L 31/18* (2006.01)

(52) U.S. Cl.
CPC ...... *A61F 2/966* (2013.01); *A61F 2002/9665* (2013.01); *A61F 2250/0071* (2013.01); *A61L 31/18* (2013.01)

(58) Field of Classification Search
CPC .............. A61F 2/966; A61F 2002/9665; A61F 2250/0071; A61F 2250/0098; A61F 2/95;
(Continued)

(56) References Cited

U.S. PATENT DOCUMENTS

| 2002/0004676 A1 | 1/2002 | Wallace et al. |
| 2004/0064179 A1 | 4/2004 | Linder et al. |

(Continued)

FOREIGN PATENT DOCUMENTS

| CA | 2432028 C | 4/2002 |
| WO | 99/40873 A1 | 8/1999 |

(Continued)

OTHER PUBLICATIONS

International Search Report for International Application No. PCT/CA2017/051163 dated Jan. 12, 2018.
Written Opinion of the International for International Searching Authority for International Application No. PCT/CA2017/051163 dated Jan. 12, 2018.
Office Action dated Dec. 16, 2020, from Canadian Application No. 3,038,825, 3 sheets.
(Continued)

*Primary Examiner* — Brooke Nicole Labranche
(74) *Attorney, Agent, or Firm* — Katten Muchin Rosenman LLP

(57) ABSTRACT

There is described an endovascular prosthesis delivery device. The subject endovascular prosthesis delivery device comprises a combination of a delivery frame element and a hub insert element that are secured to one another by a first retention element. At a distal portion of the delivery frame element, there is a prosthesis attachment zone for coupling to an endovascular prosthesis. When it is desired to deploy the endovascular prosthesis, the first retention element is broken in a manner to allow relative movement between the hub insert element and the delivery frame element. A pull
(Continued)

wire assembly is secured with respect to the hub insert element and comprises a pull wire which is coupled to the endovascular prosthesis in the prosthesis attachment zone of the delivery frame element. Once the first retention element is broken by the physician (this is done when the endovascular prosthesis is in the correct position for deployment), the physician can then retract the hub insert which has the effect of retracting pull wire from the prosthesis attachment zone of the delivery frame element. The endovascular prosthesis and the endovascular prosthesis delivery device are now detached from one another and the latter may be withdrawn from the patient.

20 Claims, 14 Drawing Sheets

(58) Field of Classification Search
CPC .......... A61F 2/9517; A61F 2002/9511; A61L 31/18; A61B 2017/00991; A61B 2017/12054; A61B 2090/037
See application file for complete search history.

(56) References Cited

U.S. PATENT DOCUMENTS

| | | |
|---|---|---|
| 2008/0082154 A1 | 4/2008 | Tseng et al. |
| 2009/0287292 A1 | 11/2009 | Becking et al. |
| 2010/0198250 A1 | 5/2010 | Ricci et al. |
| 2011/0190867 A1 | 4/2011 | Vonderwalde et al. |

FOREIGN PATENT DOCUMENTS

| | | |
|---|---|---|
| WO | 2012/145823 A1 | 11/2012 |
| WO | 2012/145826 A1 | 11/2012 |
| WO | 2014/066982 A1 | 5/2014 |

OTHER PUBLICATIONS

Office Action dated May 5, 2020, from Canadian Application No. 3,038,825, 5 sheets.
The extended European search report dated Jun. 16, 2020, from European Application No. 17854303.9-1113, 7 sheets.
Canadian Office Action dated Jul. 30, 2021 for Canadian Appln. No. 3,038,825.

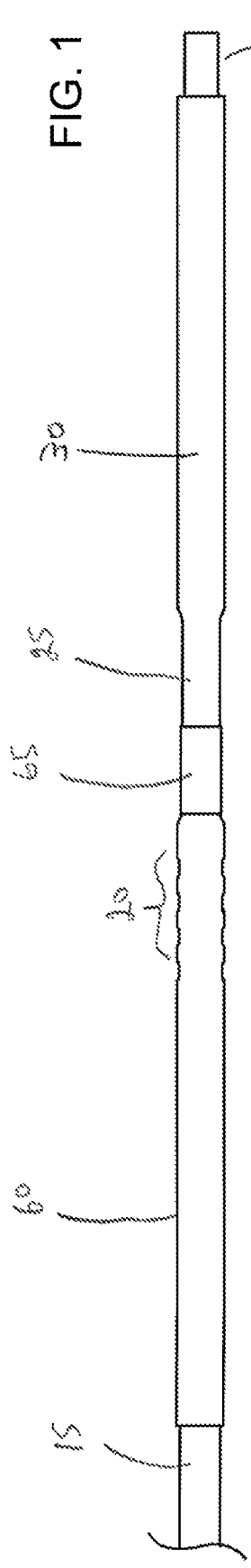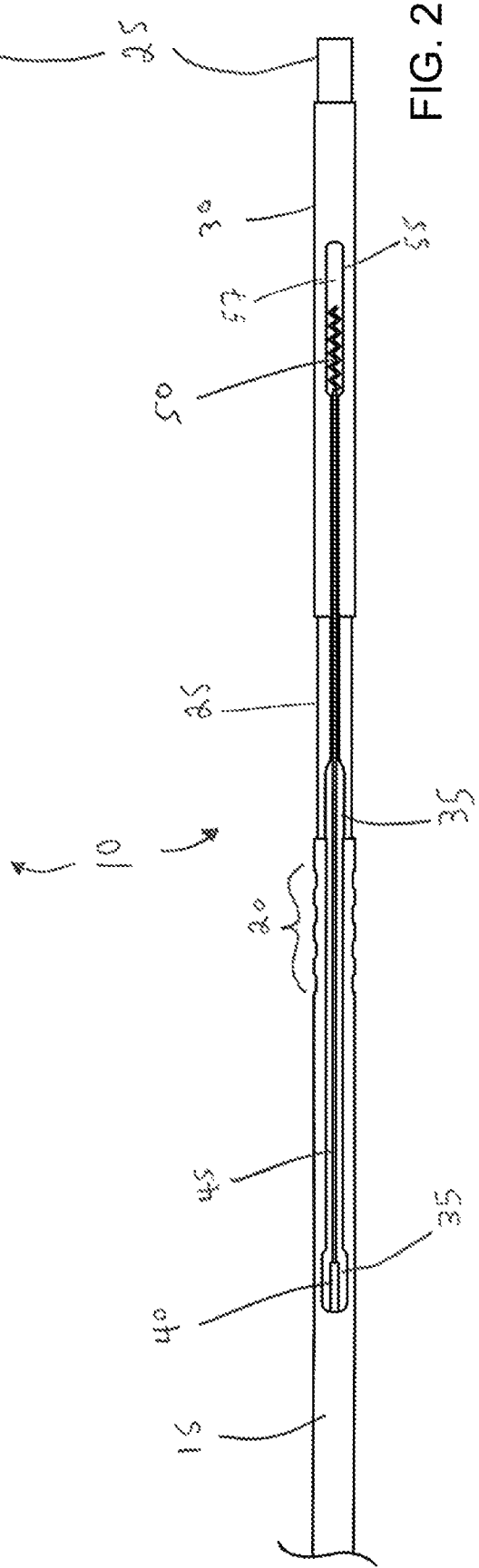

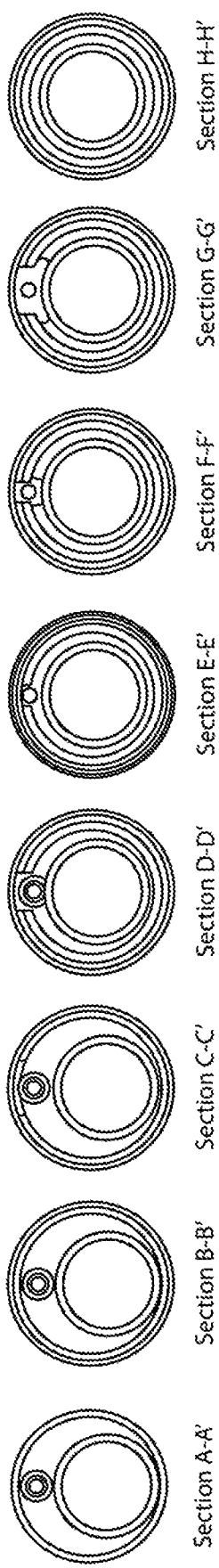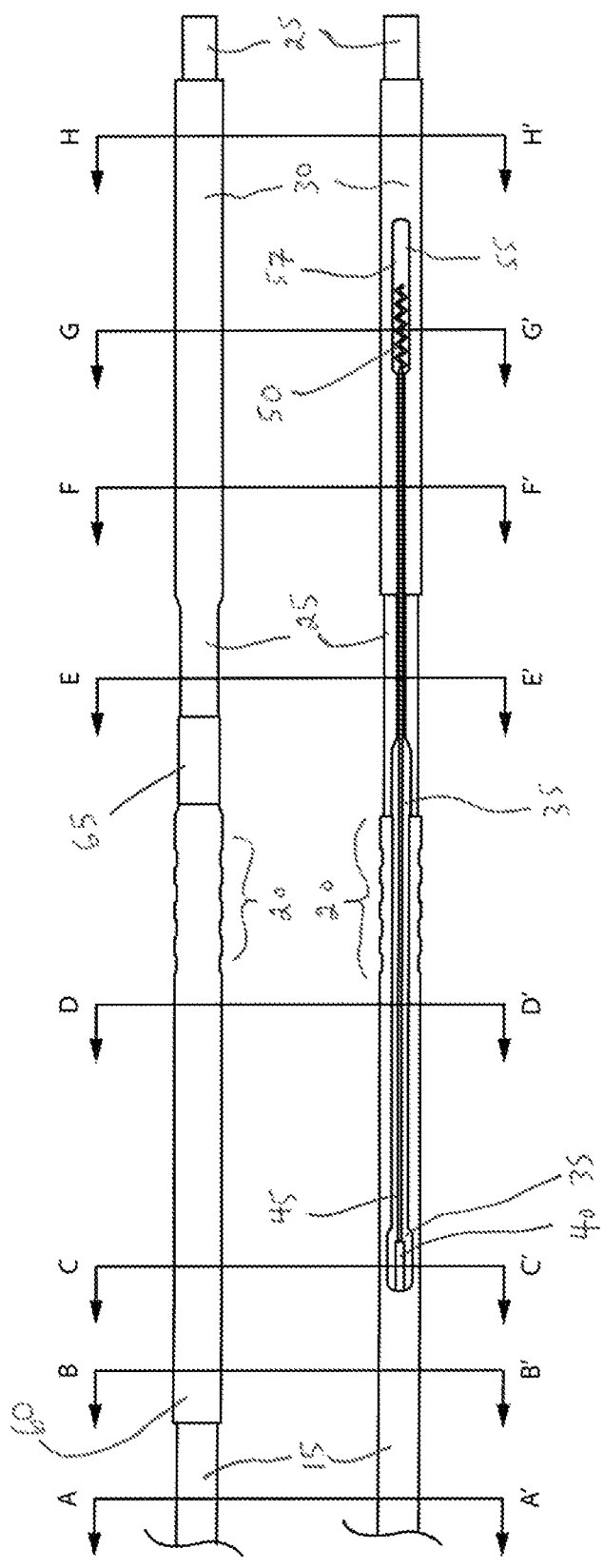
FIG. 4

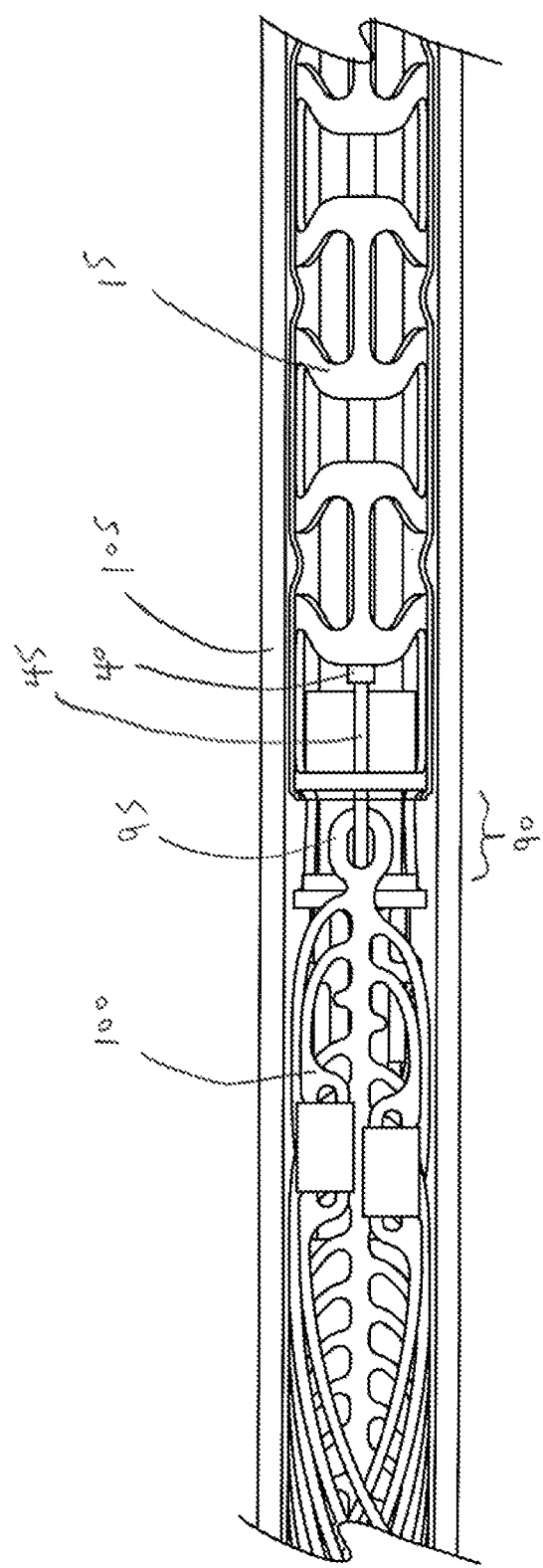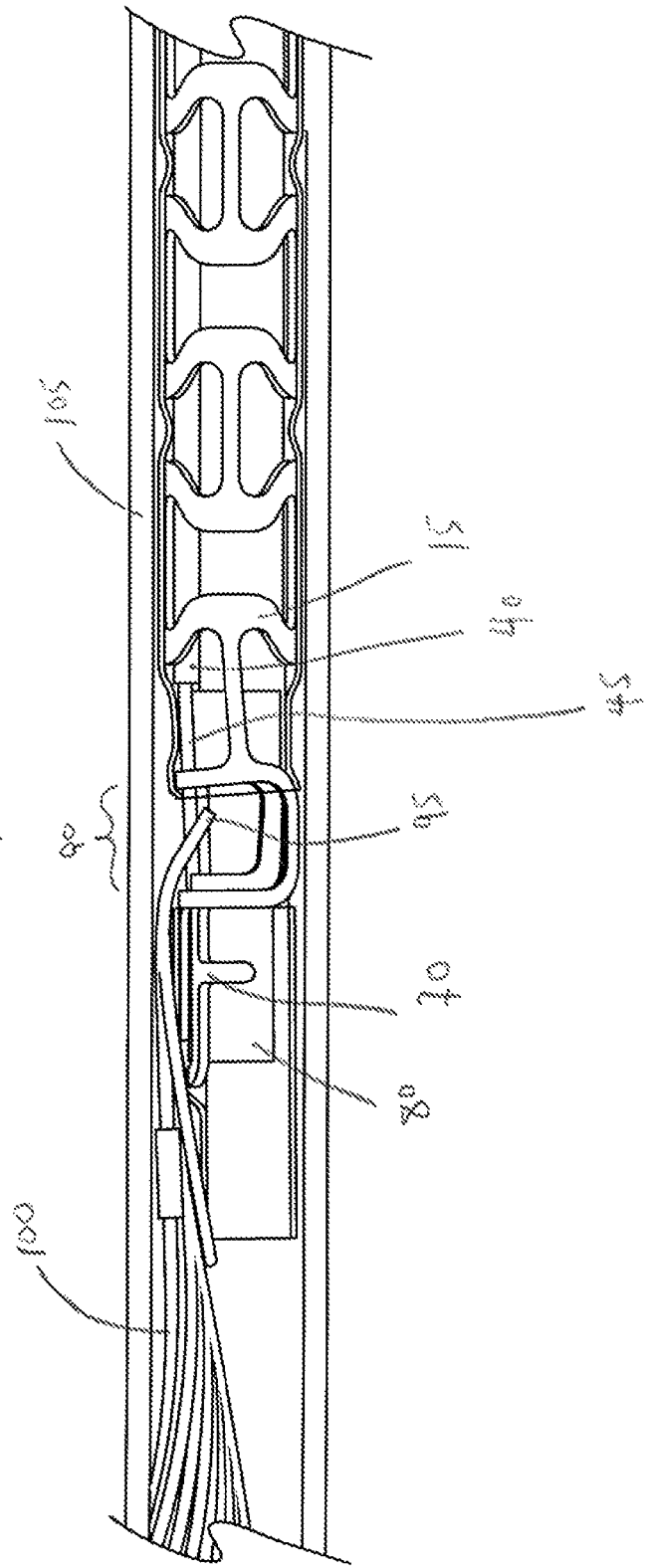

ENDOVASCULAR PROSTHESIS DELIVERY DEVICE

CROSS-REFERENCE TO RELATED APPLICATION

The present application claims the benefit under 35 U.S.C. § 119(e) of provisional patent application Ser. No. 62/495,961, filed Sep. 30, 2016, the contents of which are hereby incorporated by reference.

BACKGROUND OF THE INVENTION

Field of the Invention

In one of its aspects, the present invention relates to an endovascular prosthesis delivery device. In another of its aspects, the present invention relates to a method of treating an aneurysm in a patient. Other aspects of the invention will be apparent to those of skill in the art having in hand the present specification.

Description of the Prior Art

As is known in the art, an aneurysm is an abnormal bulging outward in the wall of an artery. In some cases, the bulging may be in the form of a smooth bulge outward in all directions from the artery—this is known as a "fusiform aneurysm". In other cases, the bulging may be in the form of a sac arising from an arterial branching point or from one side of the artery—this is known as a "saccular aneurysm".

While aneurysms can occur in any artery of the body, it is usually those which occur in the brain which lead to the occurrence of a stroke. Most saccular aneurysms which occur in the brain have a neck which extends from the cerebral blood vessel and broadens into a pouch which projects away from the vessel.

The problems caused by such aneurysms can occur in several different ways. For example, if the aneurysm ruptures, blood enters the brain or the subarachnoid space (i.e., the space closely surrounding the brain)—the latter is known as an aneurysmal subarachnoid hemorrhage. This is followed by one or more of the following symptoms: nausea, vomiting, double vision, neck stiffness and loss of consciousness. Aneurysmal subarachnoid hemorrhage is an emergency medical condition requiring immediate treatment. Indeed, 10-15% of patients with the condition die before reaching the hospital for treatment. More than 50% of patients with the condition will die within the first thirty days after the hemorrhage. Of those patients who survive, approximately half will suffer a permanent stroke. Some of these strokes occur one to two weeks after the hemorrhage itself from vasospasm in cerebral vessels induced by the subarachnoid hemorrhage. Aneurysms also can cause problems which are not related to bleeding although this is less common. For example, an aneurysm can form a blood clot within itself which can break away from the aneurysm and be carried downstream where it has the potential to obstruct an arterial branch causing a stroke (e.g., an ischemic stroke). Further, the aneurysm can also press against nerves (this has the potential of resulting in paralysis or abnormal sensation of one eye or of the face) or the adjacent brain (this has the potential of resulting in seizures).

Given the potentially fatal consequences of the aneurysms, particularly brain aneurysms, the art has addressed treatment of aneurysms using various approaches.

Generally, aneurysms may be treated from outside the blood vessels using surgical techniques or from the inside using endovascular techniques (the latter falls under the broad heading of interventional (i.e., non-surgical) techniques).

Surgical techniques usually involve a craniotomy requiring creation of an opening in the skull of the patient through which the surgeon can insert instruments to operate directly on the brain. In one approach, the brain is retracted to expose the vessels from which the aneurysm arises and then the surgeon places a clip across the neck of the aneurysm thereby preventing arterial blood from entering the aneurysm. If there is a clot in the aneurysm, the clip also prevents the clot from entering the artery and obviates the occurrence of a stroke. Upon correct placement of the clip the aneurysm will be obliterated in a matter of minutes. Surgical techniques are the most common treatment for aneurysms. Unfortunately, surgical techniques for treating these conditions are regarded as major surgery involving high risk to the patient and necessitate that the patient have strength even to have a chance to survive the procedure.

As discussed above, endovascular techniques are non-surgical techniques and are typically performed in an angiography suite using a catheter delivery system. Specifically, known endovascular techniques involve using the catheter delivery system to pack the aneurysm with a material which prevents arterial blood from entering the aneurysm—this technique is broadly known as embolization. One example of such an approach is the Guglielmi Detachable Coil which involves intra-aneurysmal occlusion of the aneurysm via a system which utilizes a platinum coil attached to a stainless steel delivery wire and electrolytic detachment. Thus, once the platinum coil has been placed in the aneurysm, it is detached from the stainless steel delivery wire by electrolytic dissolution. Specifically, the patient's blood and the saline infusate act as the conductive solutions. The anode is the stainless steel delivery wire and the cathode is the ground needle which is placed in the patient's groin. Once current is transmitted through the stainless steel delivery wire, electrolytic dissolution will occur in the uninsulated section of the stainless steel detachment zone just proximal to the platinum coil (the platinum coil is of course unaffected by electrolysis). Other approaches involve the use of materials such as cellulose acetate polymer to fill the aneurysm sac. While these endovascular approaches are an advance in the art, they are disadvantageous. Specifically, the risks of these endovascular approaches include rupturing the aneurysm during the procedure or causing a stroke (e.g., an ischemic stroke) due to distal embolization of the device or clot from the aneurysm. Additionally, concern exists regarding the long term results of endovascular aneurysm obliteration using these techniques. Specifically, there is evidence of intra-aneurysmal rearrangement of the packing material and reappearance of the aneurysm on follow-up angiography.

One particular type of brain aneurysm which has proven to be very difficult to treat, particularly using the surgical clipping or endovascular embolization techniques discussed above occurs at bifurcations, where a parent artery branches into two smaller branch arteries. An example of this type of aneurysm is one that occurs at the terminal bifurcation of the basilar artery. Successful treatment of bifurcation aneurysms (e.g., using a surgical clip) is very difficult due, at least in part, to the imperative requirement that all the brainstem perforating vessels be spared during surgical clip placement.

Unfortunately, there are occasions when the size, shape and/or location of an aneurysm make both surgical clipping and endovascular embolization not possible for a particular patient. Generally, the prognosis for such patients is not good.

Accordingly, while the prior art has made advances in the area of treatment of aneurysms, there is still room for improvement, particularly in endovascular embolization since it is such an attractive alternative to major surgery.

In International Publication Number WO 99/40873 [Marotta et al. (Marotta)], published Aug. 19, 1999, there is taught a novel endovascular approach useful in blocking of an aneurysmal opening, particularly those in saccular aneurysms, leading to obliteration of the to aneurysm. The approach is truly endovascular in that, with the endovascular prosthesis taught by Marotta, there is no requirement to pack the aneurysmal sac with a material (e.g., such is used with the Guglielmi Detachable Coil). Rather, the endovascular prosthesis taught by Marotta operates on the basis that it serves to block the opening to the aneurysmal sac thereby obviating the need for packing material. Thus, the endovascular prosthesis taught by Marotta is an important advance in the art since it obviates or mitigates many of the disadvantages of the prior art. The endovascular prosthesis taught by Marotta comprises a leaf portion capable of being urged against the opening of the aneurysm thereby closing the aneurysm. In the endovascular prosthesis taught by Marotta, the leaf portion is attached to, and independently moveable with respect to, a body comprising at least one expandable portion. The expandable portion is expandable from a first, unexpanded state to a second, expanded state with a radially outward force thereon. Thus, the body serves the general purpose of fixing the endovascular prosthesis in place at a target body passageway or vascular lumen in the vicinity at which the aneurysmal opening is located and the leaf portion serves the purpose of sealing the aneurysmal opening thereby leading to obliteration of the aneurysm. Thus, as taught by Marotta, the leaf portion functions and moves independently of the body of the endovascular prosthesis.

International Publication Numbers WO 2012/145823A1 and WO 2012/145826 [both in the name of Tippett et al. (Tippett)] teach an endovascular prosthesis and an endovascular prosthesis delivery device. The endovascular prosthesis disclosed by Tippett is an improvement over the endovascular device disclosed by Marrotta in that the former is designed to allow the physician to be able to retrieve the device so that it may be repositioned for optimum placement prior to final deployment. The endovascular prosthesis delivery device disclosed by Tippett can take the form of a number of different embodiments. In each case, it is necessary to adopt a relatively complicated system of wires to attach/detach the endovascular prosthesis to/from the delivery device—see, for example, FIGS. 4, 7, 8, 11, 12, 14, 15, 22-24, 27 and 30-35. The result is that manufacture of the kit containing the endovascular prosthesis and delivery device is relatively complex and expensive. In addition, successful implantation of the endovascular prosthesis can be more difficult with the "fish lure" arrangement illustrated in the embodiments of the delivery device disclosed by Tippett.

Accordingly, there remains a need in the art for an endovascular prosthesis delivery device that may that is relatively simple to manufacture and use to deliver and implant and endovascular prosthesis. It would be highly advantageous if relatively simple and reliable mechanism was available to detach the endovascular prosthesis from the delivery device.

SUMMARY OF THE INVENTION

It is an object of the present invention to obviate or mitigate at least one of the above-mentioned disadvantages of the prior art.

It is another object of the present invention to provide a novel endovascular prosthesis delivery device.

Accordingly, in one of its aspects, the present invention provides an endovascular prosthesis delivery device comprising:

(a) a hub insert element disposed near a proximal portion of the delivery device.

(b) a delivery frame element disposed near a distal portion of the delivery device and exteriorly with respect to at least a portion of the hub insert element, a distal portion of the delivery frame element comprising a prosthesis attachment zone;

(c) a pull wire assembly secured with respect to the hub insert element and disposed interiorly with respect to the delivery frame element, the pull wire assembly comprising a pull wire having a distal portion disposed in the prosthesis attachment zone for attachment to a prosthesis; and (d) a first retention element configured to secure (and preferably disposed exteriorly with respect to) at least a portion of the hub insert element and at least a portion of the delivery frame element to one another;

wherein the first retention element is configured to: (i) secure the hub insert element with respect to the delivery frame element during delivery of the prosthesis, and (ii) be breakable to allow for relative movement of the hub insert element and the delivery frame element to release the prosthesis from the pull wire.

In another of its aspects, the present invention provides an endovascular prosthesis delivery device comprising:

a tubular member having a distal portion and a proximal portion, the tubular member comprising a first lumen configured to receive a guidewire and a second lumen configured to receive a pull wire, a distal portion of the tubular member comprising a prosthesis attachment zone;

a hub insert element in a telescoping relationship with respect to the tubular member;

a pull wire disposed in the second lumen for attachment to a prosthesis; and a first retention element configured to secure (and preferably disposed exteriorly with respect to) at least a portion of the hub insert element and at least a portion of the tubular member with respect to one another;

wherein the first retention element is configured to: (i) secure the hub insert element with respect to the tubular member during delivery of the prosthesis, and (ii) be breakable to allow for relative movement of the hub insert element and the tubular member to release the prosthesis from the pull wire.

Thus, the present inventors have developed a novel endovascular prosthesis delivery device. The subject endovascular prosthesis delivery device comprises a combination of a delivery frame element and a hub insert element that are secured to one another by a first retention element. At a distal portion of the delivery frame element, there is a prosthesis attachment zone for coupling to an endovascular prosthesis. When it is desired to deploy the endovascular prosthesis, the first retention element is broken in a manner to allow relative movement between the hub insert element and the delivery frame element. A pull wire assembly is secured with respect to the hub insert element and comprises a pull wire which is coupled to the endovascular prosthesis in the prosthesis attachment zone of the delivery frame element. Once the first retention element is broken by the physician (this is done when the endovascular prosthesis is in the correct position for deployment), the physician can then retract the hub insert which has the effect of retracting pull wire from the prosthesis attachment zone of the delivery frame element. The endovascular prosthesis and the endovascular prosthesis delivery device are now detached from one another and the latter may be withdrawn from the patient.

The present endovascular prosthesis delivery device is believed to be a significant improvement over the one described in Tippett #1. Specifically, the present endovascular prosthesis delivery device can be more reliably produced than the "fish lure" arrangement illustrated in the above-mentioned embodiments of the delivery device disclosed by Tippett #1. In addition, the present endovascular delivery device is believed to be more reliable in deployment of the endovascular prosthesis in that, unlike the "fish lure" arrangements illustrated in the above-mentioned embodiments of the delivery device disclosed by Tippett #1, it is not necessary with the present endovascular prosthesis to rely on multiple unlooping of a "fish lure" arrangement to reliably detach the endovascular prosthesis from the delivery device. This is very important since, once the endovascular prosthesis is in correct position for deployment, the physician needs to be able to deploy/detach the device with little or no delay since a significant delay can result in the endovascular prosthesis moving from an optimal position prior to actual deployment. The present endovascular prosthesis delivery device is believed to obviate or mitigate the occurrence of such a problem.

BRIEF DESCRIPTION OF THE DRAWINGS

Embodiments of the present invention will be described with reference to the accompanying drawings, wherein like reference numerals denote like parts, and in which:

FIG. 1 illustrates a side elevation of a proximal portion of a preferred embodiment of the present endovascular prosthesis delivery device;

FIG. 2 is similar to FIG. 1 with the difference being that an element (breakaway hub heatshrink polymer 60) in the illustration in FIG. 1 is removed in FIG. 2 and the interior of the device is shown in FIG. 2;

FIG. 4 illustrates sectional views of the proximal portion of the endovascular prosthesis delivery device illustrated in FIGS. 1-2;

FIG. 10 illustrates a top view, partially cut away, of a sheathed endovascular prosthesis attached to the endovascular prosthesis delivery device illustrated in FIGS. 1-9;

FIG. 11 illustrates a side elevation, partially cut away, of a sheathed endovascular prosthesis attached to the endovascular prosthesis delivery device illustrated in FIGS. 1-9;

DETAILED DESCRIPTION OF THE PREFERRED EMBODIMENTS

Figure 3:
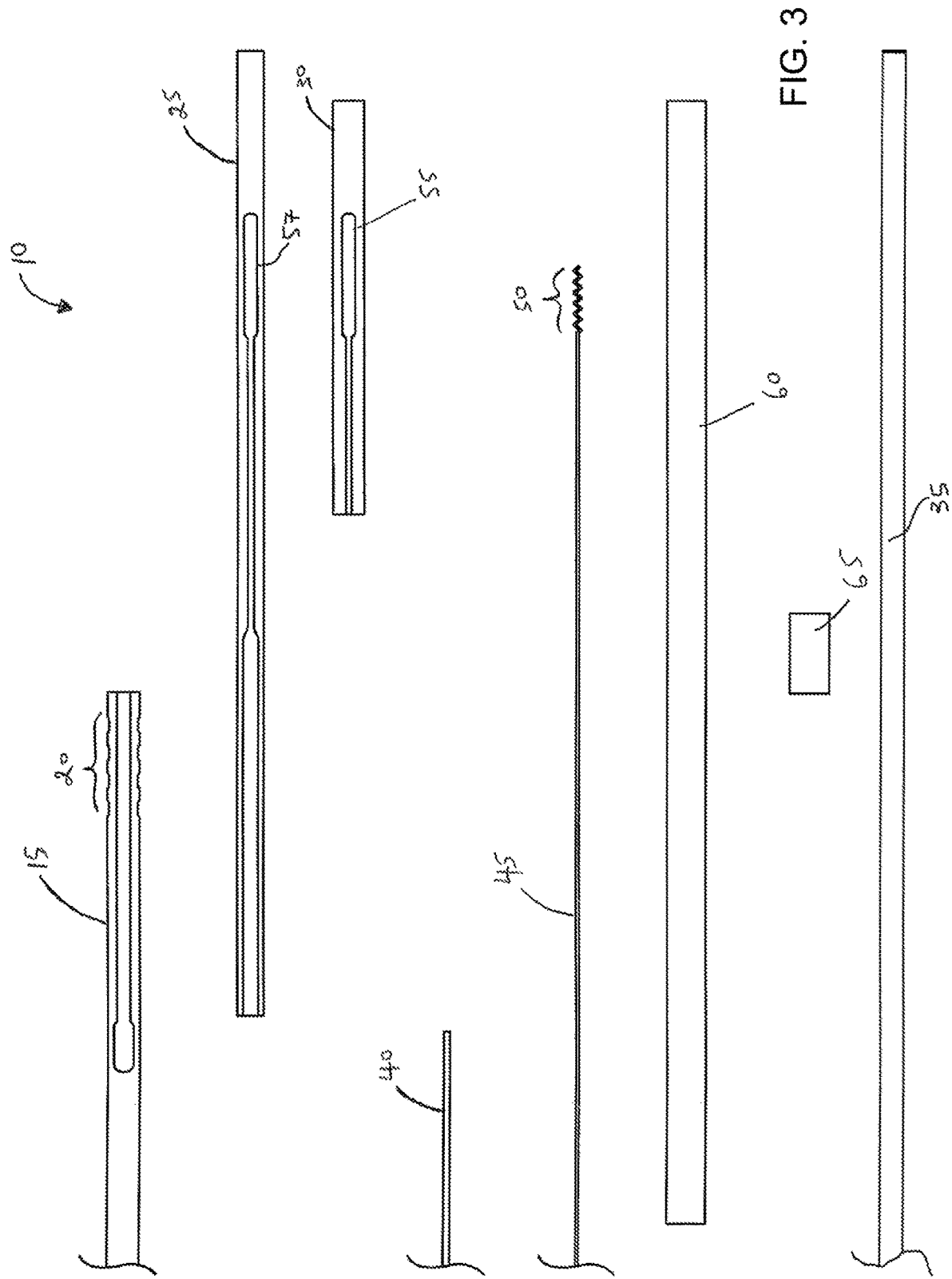
FIG. 3 illustrates an exploded view in side elevation of the various elements of the device shown in FIG. 1.

In a first aspect, the present invention relates to an endovascular prosthesis delivery device comprising: (a) a hub insert element disposed near a proximal portion of the delivery device, (b) a delivery frame element disposed near a distal portion of the delivery device and exteriorly with respect to at least a portion of the hub insert element, a distal portion of the delivery frame element comprising a prosthesis attachment zone; (c) a pull wire assembly secured with respect to the hub insert element and disposed interiorly with respect to the delivery frame element, the pull wire assembly comprising a pull wire have a distal portion disposed in the prosthesis attachment zone for attachment to a prosthesis; and (d) a first retention element configured to secure (and preferably disposed exteriorly with respect to) at least a portion of the hub insert element and at least a portion of the delivery frame element to one another; wherein the first retention element is configured to: (i) secure the hub insert element with respect to the delivery frame element during delivery of the prosthesis, and (ii) be breakable to allow for relative movement of the hub insert element and the delivery frame element to release the prosthesis from the pull wire.

In a second aspect, the present invention relates to an endovascular prosthesis delivery device comprising: a tubular member having a distal portion and a proximal portion, the tubular member comprising a first lumen configured to receive a guidewire and a second lumen configured to receive a pull wire, a distal portion of the tubular member comprising a prosthesis attachment zone; a hub insert element in a telescoping relationship with respect to the tubular member; a pull wire disposed in the second lumen for attachment to a prosthesis; and a first retention element configure to secure (and preferably disposed exteriorly with respect to) at least a portion of the hub insert element and at least a portion of the tubular member with respect to one another; wherein the first retention element is configured to: (i) secure the hub insert element with respect to the tubular member during delivery of the prosthesis, and (ii) be breakable to allow for relative movement of the hub insert element and the tubular member to release the prosthesis from the pull wire.

Preferred embodiments either of this first aspect or second aspect of the present endovascular prosthesis delivery device may include any one or a combination of any two or more of any of the following features:

- the endovascular prosthesis delivery device further comprises a tubular member configured to receive a guidewire, the tubular member being disposed interiorly with respect to the hub insert element;
- the pull wire assembly further comprises a pull wire sleeve in which the pull wire is disposed;
- the pull wire sleeve has a distal end disposed proximally with respect to the prosthesis attachment zone;
- the pull wire sleeve has a proximal end disposed distally with respect to the hub insert element;

the pull wire sleeve has a proximal end disposed distally with respect to a proximal portion of the delivery frame element;

the pull wire sleeve has an inner surface comprising a polymer lining;

the pull wire sleeve has an inner surface comprising a polymer lining have a low coefficient of friction with respect to the pull wire;

the pull wire sleeve has an inner surface comprising a lining comprising polytetrafluoroethylene (PTFE);

the pull wire sleeve is secured with respect to the tubular member by a compressive force of the delivery frame element;

the pull wire sleeve is secured with respect to the tubular member by an adhesive;

the pull wire sleeve is secured with respect to the tubular member by the combination of a compressive force of the delivery frame element and an adhesive;

the first retention element comprises a flexible material;

the first retention element comprises a flexible polymer material;

the first retention element comprises a flexible material that has been subjected to heat shrinking;

the first retention element comprises a flexible polymer material that has been subjected to heat shrinking;

the delivery frame element comprises at least one retention window element;

the first retentional element is at least partially embedded in at least one retention window element disposed in the delivery frame element;

the first retentional element is at least partially embedded in a plurality of retention window elements disposed in the delivery frame element;

the first retentional element and the retention window element combined to form a corrugated portion;

the endovascular prosthesis delivery device further comprises a visual marker element disposed exteriorly of the first retention element;

the visual marker element is disposed proximally with respect to the pull wire sleeve;

the visual marker element is disposed proximally with respect to the delivery frame element;

the endovascular prosthesis delivery device further comprises a tip collar element secured to the tubular member distally or proximally with respect to the prosthesis attachment zone;

the endovascular prosthesis delivery device further comprises a tip collar element secured to the tubular member distally and proximally with respect to the prosthesis attachment zone;

the tip collar element comprises an opening in substantial alignment with the prosthesis attachment zone;

the tip collar element comprises a channel configured to receive a distal portion of the pull wire;

the channel is defined by a pair of opposed side portions;

the channel is defined by a pair of opposed side portions the distal ends of which are interconnected by an end portion configured to substantially prevent axial movement of the pull wire toward the distal portion of the tubular member;

a distal portion of the delivery frame element comprises a protrusion portion configured to cover at least a portion of the channel;

the endovascular prosthesis delivery device further comprises a second retention element disposed distally with respect to the prosthesis attachment zone and exteriorly with respect to at least a portion of the tubular member and at least a portion of the tip collar element;

the second retention element comprises a flexible material;

the second retention element comprises a flexible polymer material;

the second retention element comprises a flexible material that has been subjected to heat shrinking;

the second retention element comprises a flexible polymer material that has been subjected to heat shrinking;

the endovascular prosthesis delivery device further comprises a radioopaque marker disposed in a distal portion thereof;

the endovascular prosthesis delivery device further comprises a radioopaque marker at least a portion of which is disposed distally with respect to the prosthesis attachment zone;

the radioopaque marker is in the form of a foil element;

the radioopaque marker is disposed exteriorly with respect to the tubular member;

the prosthesis attachment zone is configured to permit rotational movement of an endovascular prosthesis with respect to longitudinal axis of delivery system;

the distal end of the pull wire is proximal to the distal end of the tubular member;

the proximal portion of tubular member is the most proximal portion of delivery system;

the hub insert element comprises a slot portion in at least a portion of its length, the slot portion configured to receive a proximal portion of the pull wire;

the endovascular prosthesis delivery device further comprises a hub collar element disposed exteriorly with respect a proximal portion of the hub insert element;

the distal portion of the hub collar element is in spaced relation with respect to the proximal portion of the delivery frame element;

the hub insert element and the hub collar element each comprises a slot portion in substantial alignment with one another and configured to received a proximal portion of the pull wire;

the slot comprises an adhesive to adhere the hub insert, the hub collar element and the proximal portion of the pull wire assembly;

the device further comprises an adhesive for securing the hub insert element and the hub collar element; and/or the first retention element extends along less than 50%, preferably less than 40%, more preferably less than 30%, even more preferably less than 20, most preferably less than 10%, of a longitudinal length of the endovascular prosthesis delivery device.

With reference to FIGS. 1-2, there is illustrated a proximal portion 10 of a preferred embodiment of the present endovascular prosthesis delivery device.

The components in FIGS. 1 and 2 can be easily understood with reference to FIG. 3 which illustrates the components in an exploded view in relative alignment along a longitudinal axis of proximal portion 10 of the endovascular prosthesis delivery device:

| Reference Numeral | Component |
| --- | --- |
| 15 | delivery system frame |
| 20 | heatshrink retention windows |
| 25 | insert hub |
| 30 | hub collar |
| 35 | guidewire tubing |

-continued

| Reference Numeral | Component |
|---|---|
| 40 | pull wire tube |
| 45 | pull wire |
| 50 | proximal portion of pull wire 45 |
| 55 | interior cavity of hub collar 30 |
| 57 | interior cavity of hub insert 25 |
| 60 | breakaway hub heatshrink polymer |
| 65 | visual marker |

| Reference Numeral | Component |
|---|---|
| 15 | delivery system frame |
| 17 | tab element |
| 35 | guidewire tubing |
| 40 | pull wire tube |
| 45 | pull wire |
| 62 | flexible heatshrink polymer |
| 70 | tip collar |
| 75 | channel in tip collar element 70 |
| 80 | radioopaque marker |
| 85 | distal heatshrink polymer |
| 90 | prosthesis attachment window |

Thus, with initial reference to FIG. 3, proximal portion 10 of the endovascular prosthesis delivery device comprises a delivery system frame 15. This element is similar to the delivery system device disclosed in Tippett #1 except for the distal portion thereof which will be described in more detail below. Delivery system frame 15 comprises a region of heatshrink retention windows 20, the purpose of which will be described below.

The proximal portion of delivery system frame 15 is placed over a distal portion of a hub insert 25. A hub collar 30 is placed over a proximal portion of hub insert 25. A pull wire tube 40 is disposed within delivery system frame 15 and a pull wire 45 is disposed within pull wire tube 40. As illustrated, a proximal portion 50 of pull wire 45 is disposed in an interior cavity 55 of hub collar 30 and an interior cavity 57 of hub insert 25. An adhesive (not shown for clarity) is disposed in interior cavity 55 of hub collar 30 and interior cavity 57 of hub insert 25 and serves to secure proximal portion 50 of pull wire 55 with respect to interior cavity 55 of hub collar 30 and interior cavity 57 of hub insert 25.

With reference to FIGS. 1-3, a breakaway hub heatshrink polymer 60 (also referred to as a "first retention element" elsewhere in this specification) is disposed over the previously described elements. When breakaway hub heatshrink polymer 60 is shrunk in place, heatshrink retention windows 20 improve the mechanical fixation of breakaway hub heatshrink polymer 60 to delivery system frame 15. In such a configuration, it will be understood that breakaway heatshrink 60 serves to secure system frame 15 to the combination hub insert 25 and hub collar 30—i.e., hub insert 25 and hub collar 30 are bonded to each other by an adhesive (not shown for clarity) to form a breakaway hub assembly.

A visual marker 65 is disposed on the outside of breakaway hub heatshrink 60 and serves to facilite detachment of an endovascular prosthesis as described below.

It will be appreciated by those of skill in the art, that FIG. 2 illustrates the proximal portion 10 of the present endovascular prosthesis delivery device without the presence of breakaway hub heatshrink polymer 60. Further, it will be appreciated the FIG. 2 has been labelled to denote the various elements as if breakaway hub heatshrink polymer 60 is not present.

FIG. 4 illustrates proximal portion 10 of the endovascular prosthesis delivery device illustrated in FIGS. 1-3 showing various sectional views of the components along the longitudinal axis of the endovascular prosthesis delivery device. It is believed these views are self-explanatory in light of the description of the components provided above in relation to FIGS. 1-3

Figure 7:
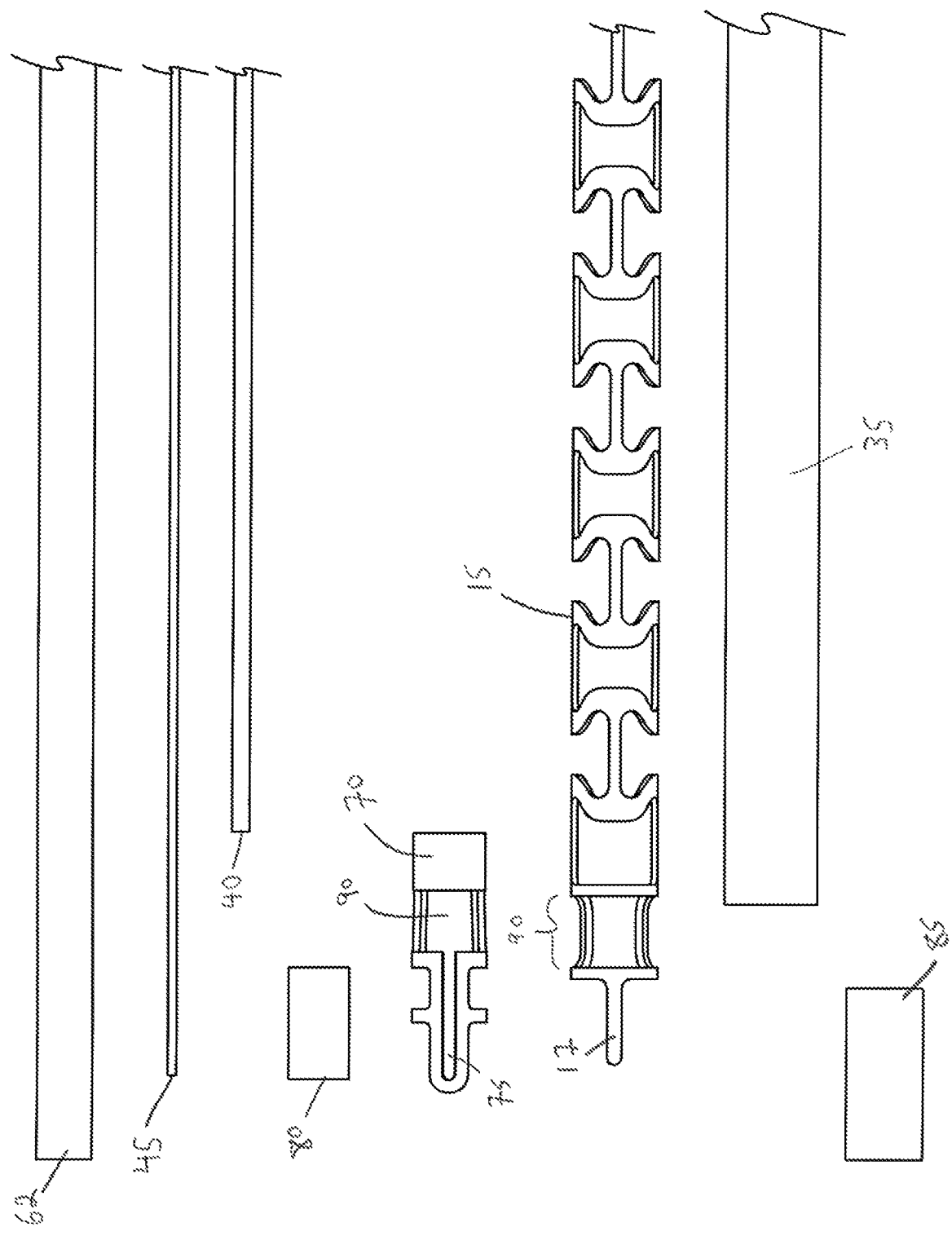
FIG. 7 illustrates an exploded view in side elevation of elements in side elevation of the the distal portion of the endovascular delivery device shown in FIGS. 5-6.
Figure 8:
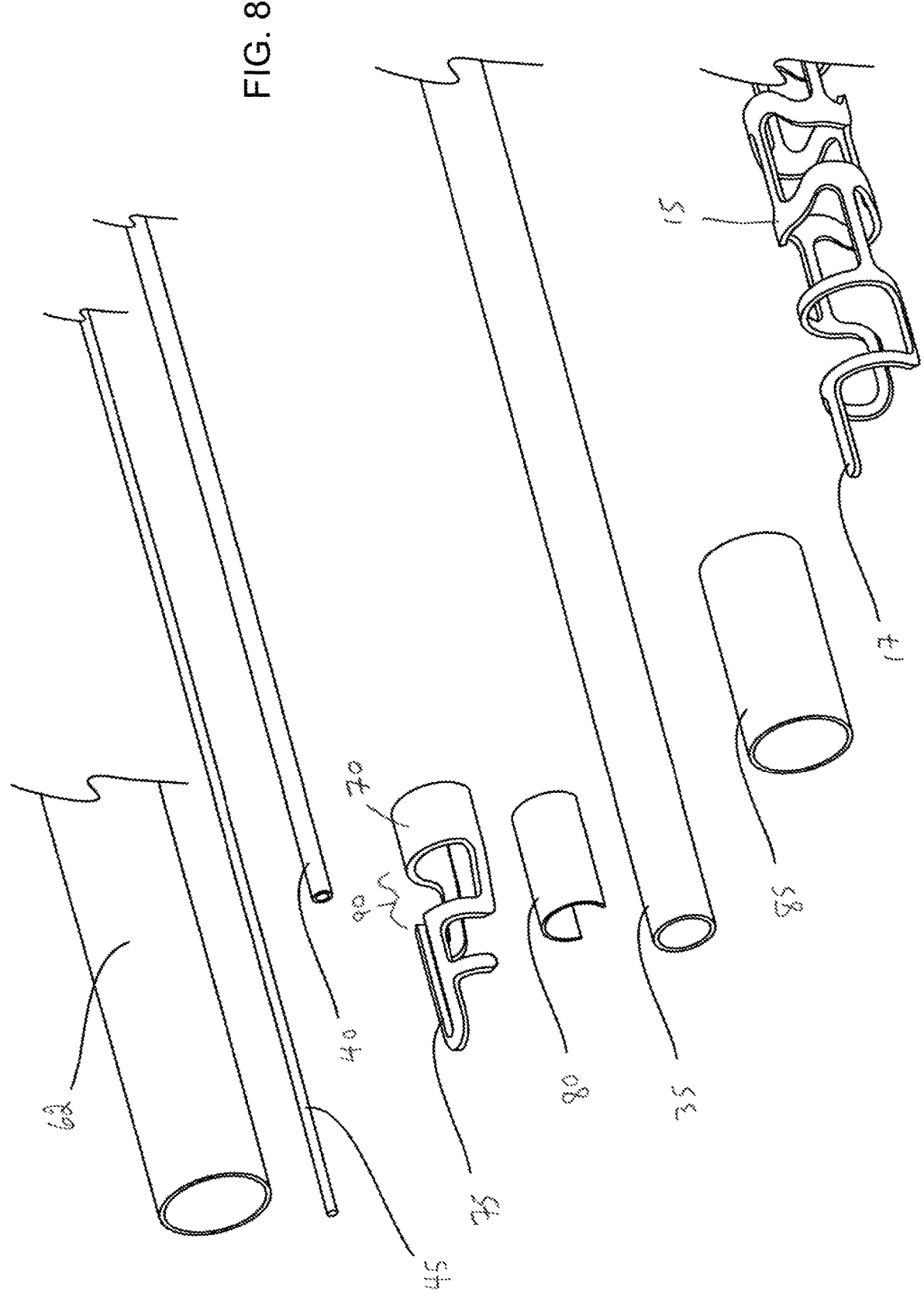
FIG. 8 illustrates an exploded view in perspective of elements in side elevation of the the distal portion of the endovascular delivery device shown in FIGS. 5-6.

With reference to FIGS. 5-9, there is illustrated a distal portion 67 of the endovascular delivery device illustrated in FIGS. 1-4, Again, the components may be understood readily with reference to FIGS. 7-8 (as will be apparent, some of these components have been identified in FIGS. 1-4):

Additionally, it can be seen that distal portion 67 of the endovascular prosthesis delivery device comprises a tip collar 70 having a groove 75, a prosthesis attachment window 90 formed in a distal portion of delivery system frame 15, a radioopaque marker 80 and a distal heatshrink polymer 85 (also referred to as a "second retention element" used elsewhere in this specification). It can also be seen that a distal-most end of delivery system frame 15 comprises a tab element 17. Distal heatshrink polymer 85 serves to secure guidewire tubing 35, tip collar 70, radioopaque marker 80 and tab element 17 of delivery system frame 15 with respect to one another.

Figure 5:
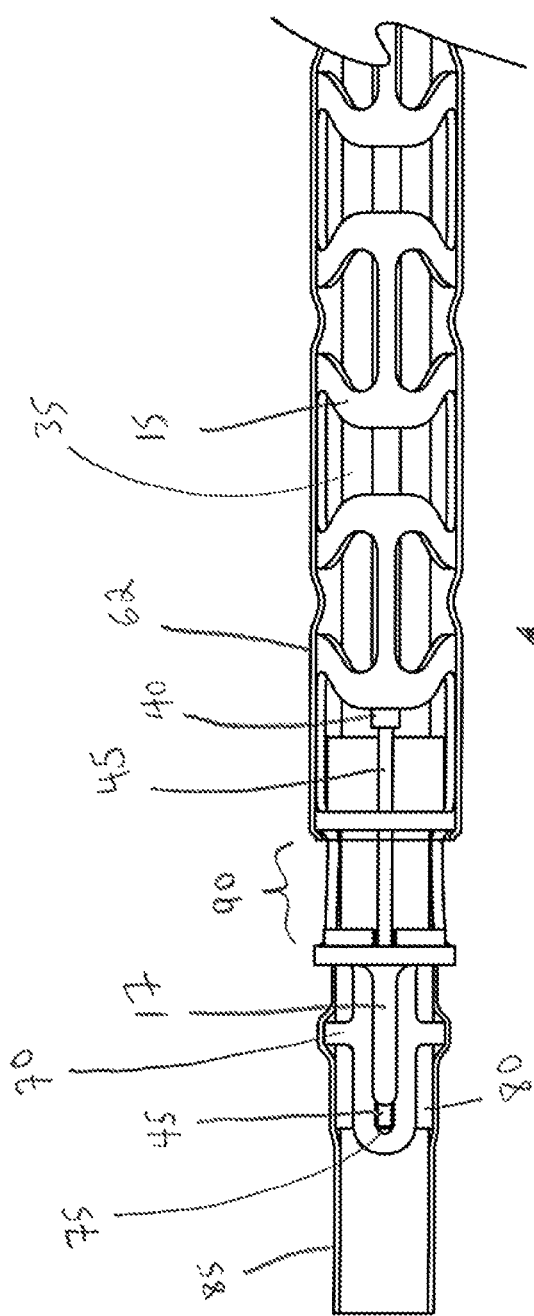
FIG. 5 illustrates a top view, partially cut away, of a distal portion of the endovascular delivery device shown in FIGS. 1-2.
Figure 6:
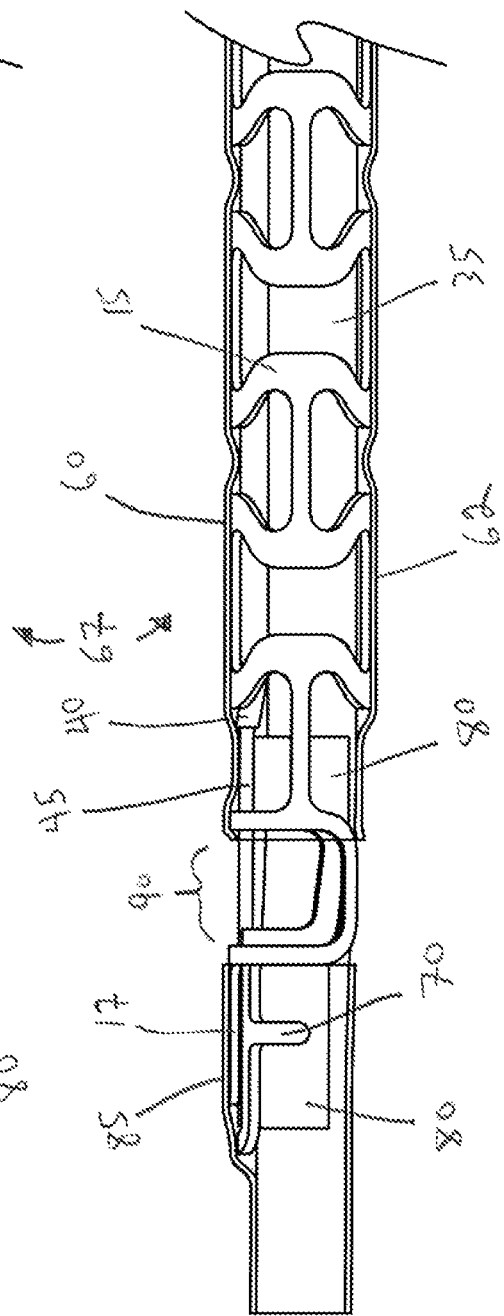
FIG. 6 illustrates a side elevation, partially cut away, of a distal portion of the endovascular delivery device shown in FIGS. 1-2.

With reference to FIG. 5, it can be seen that the distal end of pull wire 45 is disposed in groove 75 of tip collar 70. With further reference to FIG. 5, it can be seen that tab element 17 of delivery system frame 15 is disposed atop channel 75 of tip collar 70 which serves to space pullwire tube 40 and pull wire 45 away from guidewire tubing 35 thereby to permit an endovascular prosthesis 100 to pivot about pull wire 45 prior to detachment (this will be described below, particularly with reference to FIG. 12). As can be further seen with reference to FIGS. 5-6, the proximal portion of distal heatshrink polymer 85 is spaced from the distal portion of flexible heatshrink polymer 62 to expose prosthesis attachment window 90 in tip collar 70 and in which an exposed portion of pull wire 40 is disposed.

Thus, it will be apparent that the illustrated endovascular prosthesis includes three separate heatshrink polymer elements: breakaway hub heatshrink polymer 60, distal heatshrink polymer 85 and flexible heatshrink polymer 62 disposed intermediate thereof. Preferably, distal heatshrink polymer 85 has a smaller diameter than flexible heatshrink polymer 62. In a preferred embodiment, polymer used for breakaway hub heatshrink polymer 60, distal heatshrink polymer 85 and flexible heatshrink polymer 62 is polyethylene terephthalate (PET).

Figure 9:
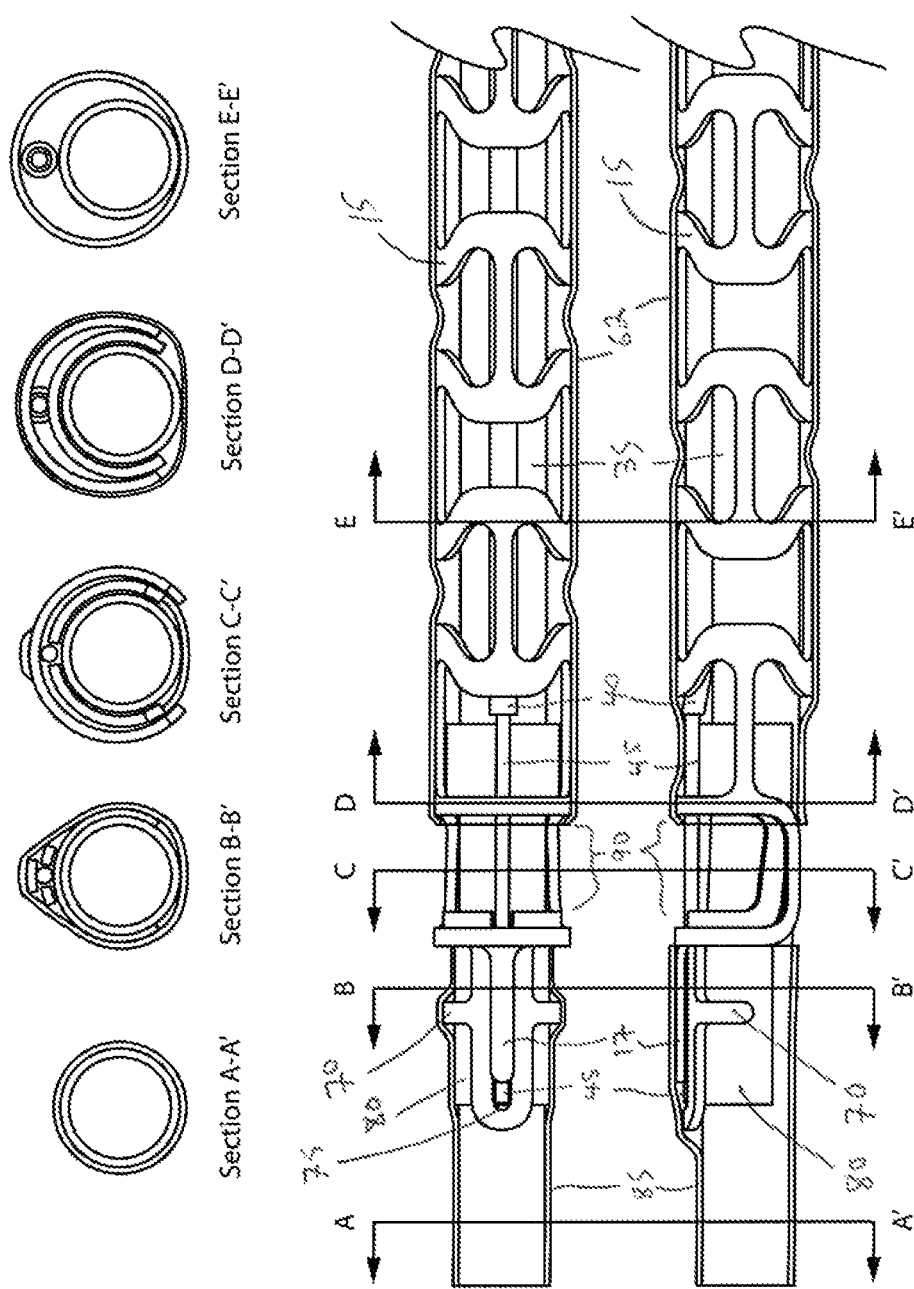
FIG. 9 illustrates sectional views of the distal portion of the endovascular prosthesis delivery device illustrated in FIGS. 5-6.

FIG. 9 illustrates the distal portion 67 of the endovascular prosthesis delivery device showing various sectional views which should be self-explanatory in light of the above discussion with reference to FIGS. 5-8.

FIGS. 10 and 11 illustrate the distal portion 67 of the endovascular prosthesis delivery device attached to a loop portion 95 of an endovascular prosthesis 100. As illustrated, a delivery sheath 105 encases the distal portion 67 of the endovascular prosthesis delivery device and endovascular prosthesis 100.

Figure 12:
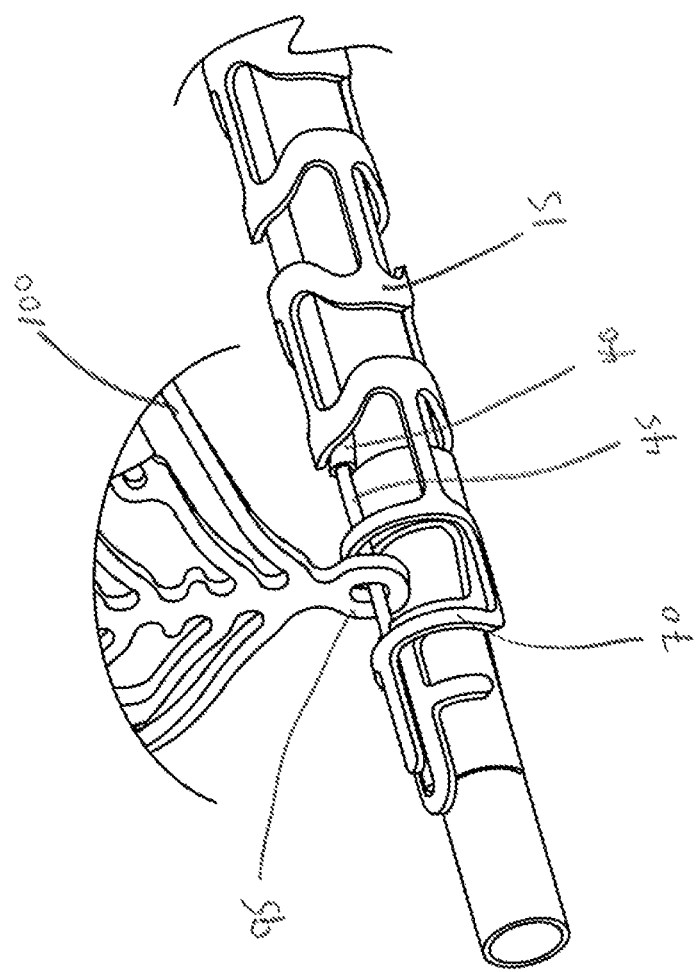
FIG. 12 is a view of the arrangement shown in FIGS. 10-11 with the sheath removed so that the endovascular prosthesis is movable while still attached to the endovascular prosthesis delivery device.
Figure 13:
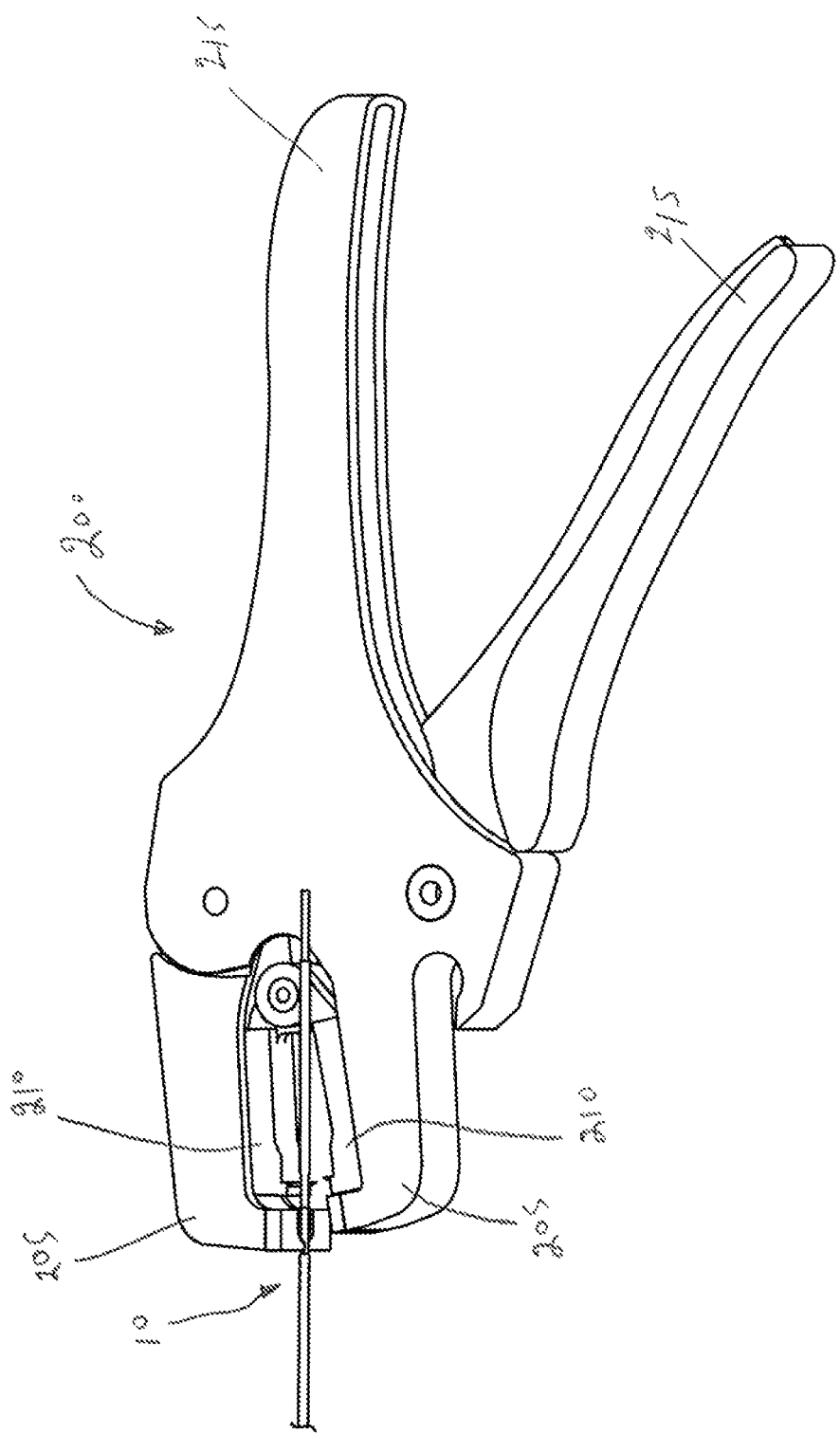
FIGS. 13-16 illustrate the use of a detacher to detach the endovascular prosthesis delivery device shown in FIGS. 10-12.
Figure 14:
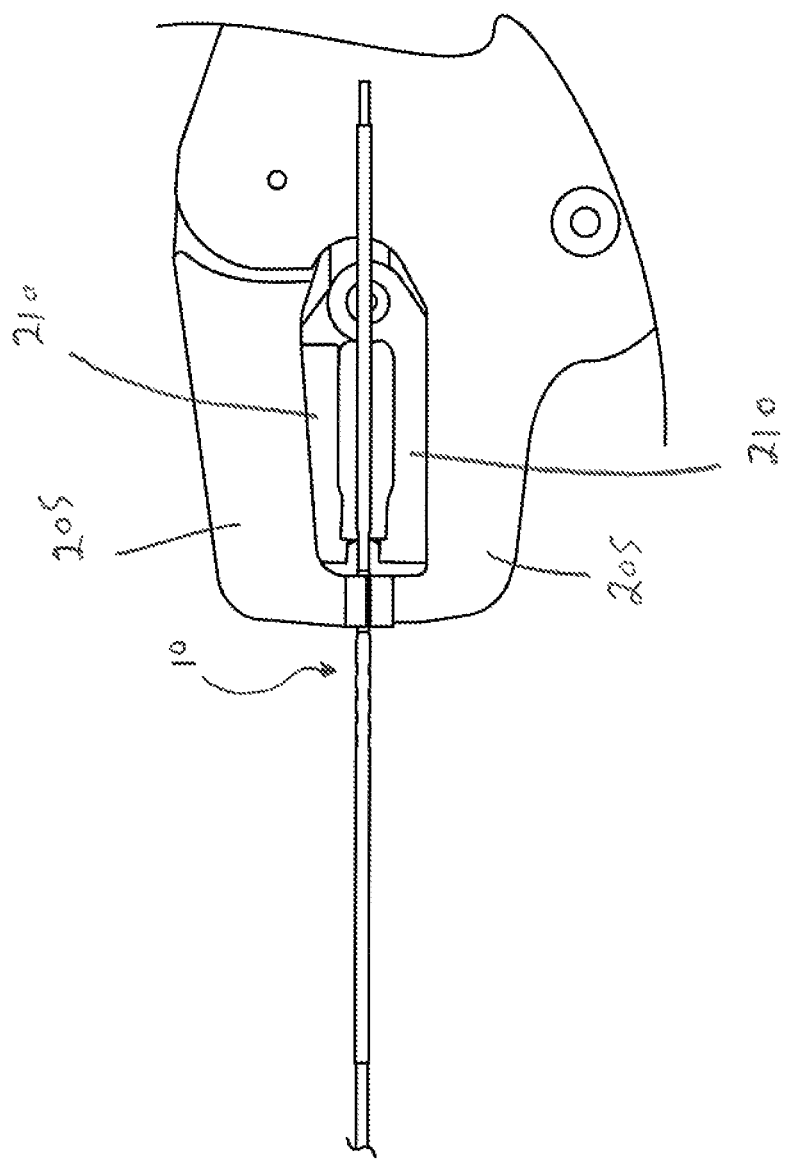
Figure 15:
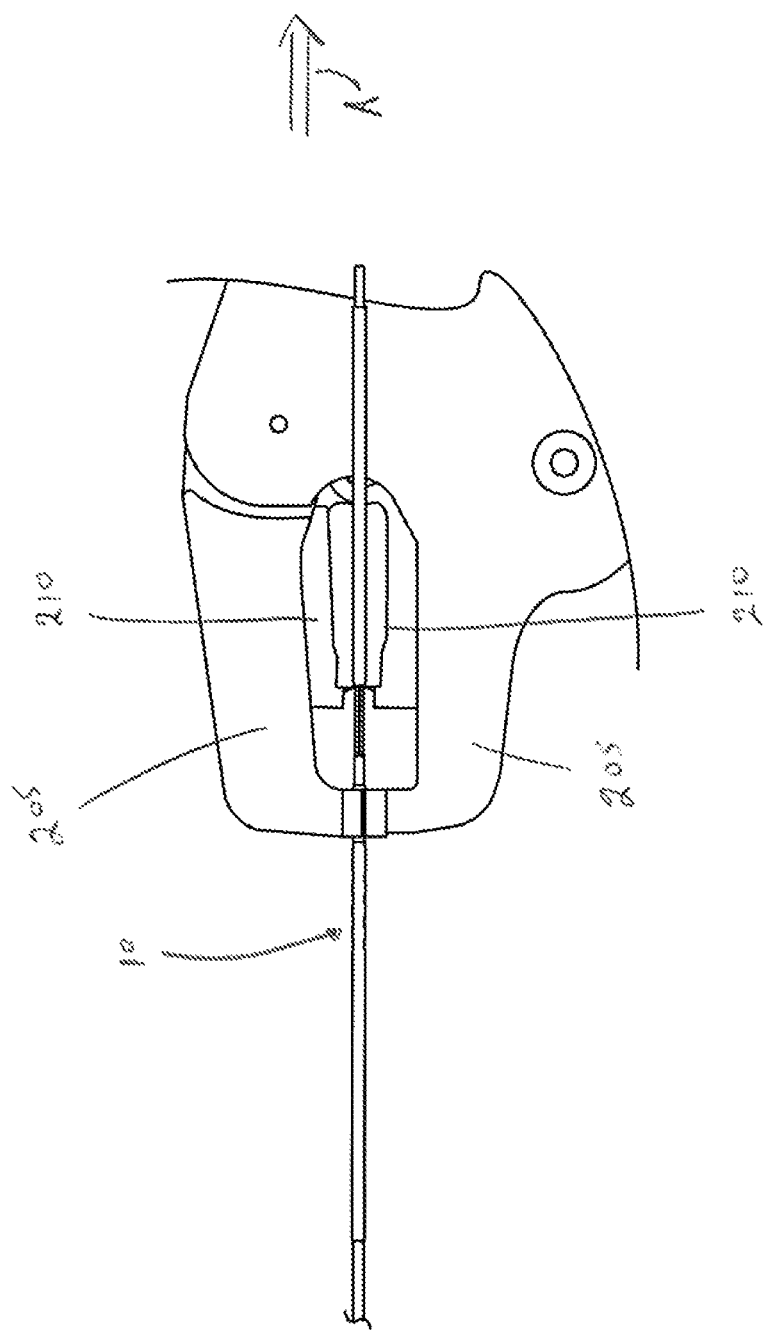
Figure 16:
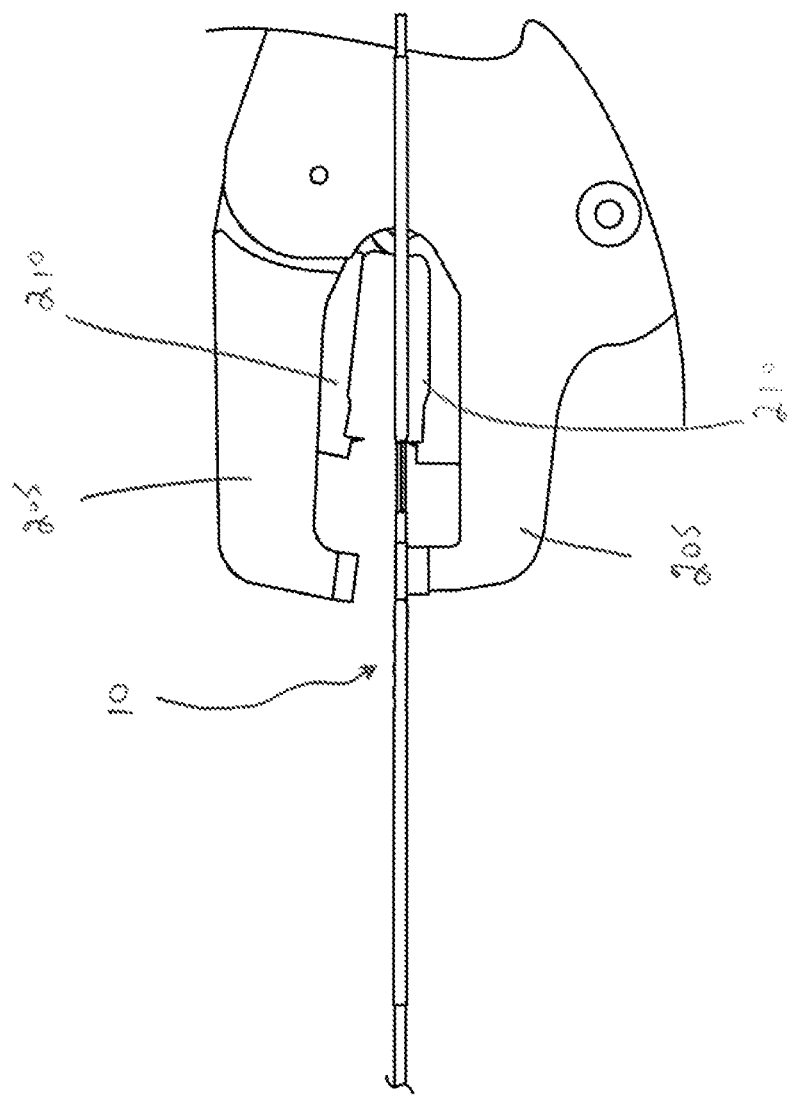
Figure 17:
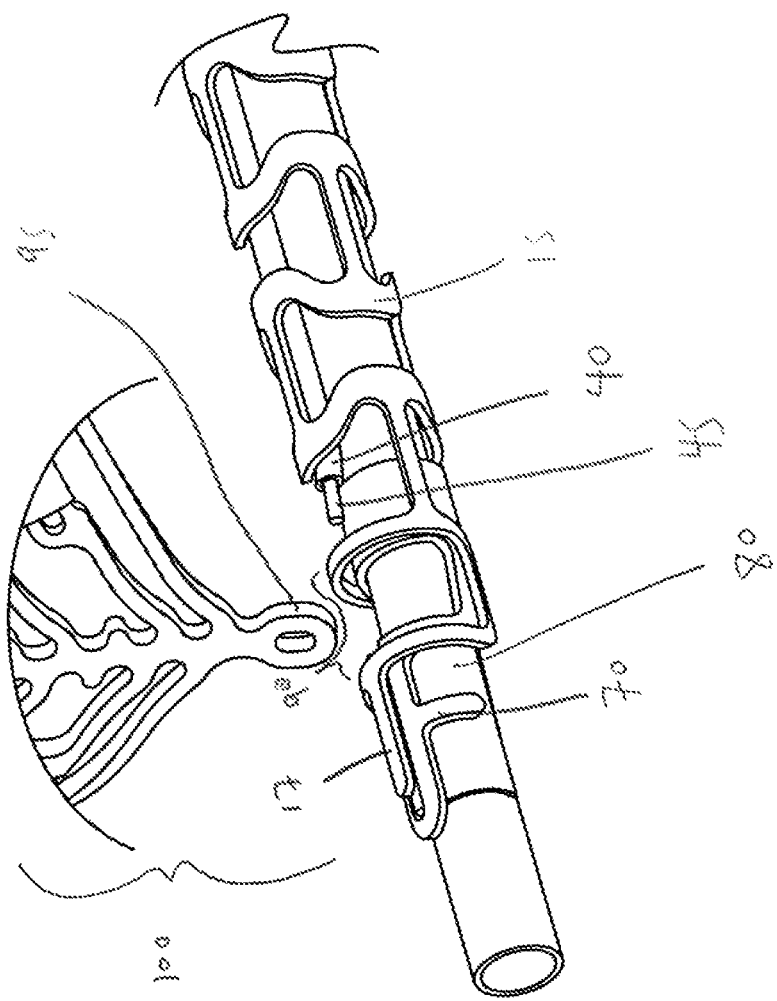
FIG. 17 illustrates detachment of the endovascular prosthesis from the endovascular prosthesis device.

FIG. 12 illustrates a portion of endovascular prosthesis 100 and the distal portion 67 of the endovascular prosthesis delivery device unsheathed (a number of elements of the distal portion 67 of the endovascular prosthesis described above with reference to FIGS. 1-11 have been omitted for clarity purposes). Those of skill in the art will understand that endovascular prosthesis 100 is rotationally movable about pull wire 45 via attachment loop 95.

Endovascular prosthesis 100 may be used with the present endovascular prosthesis delivery device to deliver endovascular prosthesis 100 to the correct position in the patient. In this regard, reference is made to Tippett #1 described above and to International Patent Publication Number WO2014/066982 [Tippet et al. ("Tippet #2)] for a disclosure of delivery of an endovascular prosthesis to the correct position in the patient using the endovascular prosthesis device taught by Tippett #1.

FIGS. 13-17 illustrate detachment of endovascular prosthesis 100 from the proximal portion 65 of the present endovascular prosthesis delivery device once the former is correctly positioned.

Thus, detacher 200 is used and comprises a pair of outer jaws 205, a pair of inner jaws 210 and a pair of grips 215.

When it is desired to detach endovascular prosthesis 100 from distal portion 67 of the present endovascular prosthesis delivery device, detacher 200 is placed such that outer jaws 205 are aligned with a portion of proximal portion 10 distal to visual marker 65 while inner jaws 210 are aligned with a portion of proximal portion 10 proximal to visual marker 65. Once so aligned, handles 215 of detacher 200 are squeezed together initially resulting in outer jaws 205 and inner jaws 210 clamping on the respective portions of proximal portion 10 of the present endovascular prosthesis delivery device—see FIG. 14. As handles 215 are continued to be squeezed, inner jaws 210 are retracted in the direction of arrow A while outer jaws 205 are held in place—see FIG. 15.

The resulting action severs (or breaks) breakaway hub heatshrink polymer 60. Such breakage results in delivery system frame 15 and hub insert 25 no longer being secured to one another and being movable in a telescoping manner. Handles 215 are then released—see FIG. 16.

The physician then grips hub insert 25 and/or hub collar 30 and retracts either or both of these elements. This has the effect of retracting pull wire 45 from prosthesis attachment window 90 in tip collar 70—see FIG. 17. At this point, endovascular prosthesis 100 is instantly detached from the distal portion 67 of the present endovascular prosthesis delivery system.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An endovascular prosthesis delivery device comprising:
    (a) a hub insert element disposed near a proximal portion of the delivery device;
    (b) a delivery frame element disposed near a distal portion of the delivery device and exteriorly with respect to at least a portion of the hub insert element, a distal portion of the delivery frame element comprising a prosthesis attachment zone;
    (c) a pull wire assembly secured with respect to the hub insert element and disposed interiorly with respect to the delivery frame element, the pull wire assembly comprising a pull wire having a distal portion disposed in the prosthesis attachment zone for attachment to a prosthesis; and
    (d) a first retention element disposed exteriorly with respect to the at least a portion of the hub insert element and at least a portion of the delivery frame element;
    wherein the first retention element is configured to: (i) secure the hub insert element with respect to the delivery frame element during delivery of the prosthesis, and (ii) be breakable to allow for relative movement of the hub insert element and the delivery frame element to release the prosthesis from the pull wire.

2. The endovascular prosthesis delivery device defined in claim 1, further comprising a tubular member configured to receive a guidewire, the tubular member being disposed interiorly with respect to the hub insert element.

3. The endovascular prosthesis delivery device defined in claim 2, further comprising a tip collar element secured to the tubular member distally and proximally with respect to the prosthesis attachment zone.

4. The endovascular prosthesis delivery device defined in claim 3, wherein the tip collar element comprises a channel configured to receive a distal portion of the pull wire.

5. The endovascular prosthesis delivery device defined in claim 1, wherein the pull wire assembly further comprises a pull wire sleeve in which the pull wire is disposed.

6. The endovascular prosthesis delivery device defined in claim 5, wherein the pull wire sleeve has a distal end disposed proximally with respect to the prosthesis attachment zone.

7. The endovascular prosthesis delivery device defined in claim 5, wherein the pull wire sleeve has a proximal end disposed distally with respect to the hub insert element.

8. The endovascular prosthesis delivery device defined in claim 5, wherein the pull wire sleeve has a proximal end disposed distally with respect to a proximal portion of the delivery frame element.

9. The endovascular prosthesis delivery device defined in claim 5, wherein the pull wire sleeve has an inner surface comprising a polymer lining.

10. The endovascular prosthesis delivery device defined in claim 5, wherein the pull wire sleeve has an inner surface comprising a polymer lining have a low coefficient of friction with respect to the pull wire.

11. The endovascular prosthesis delivery device defined in claim 5, wherein the pull wire sleeve has an inner surface comprising a lining comprising polytetrafluoroethylene (PTFE).

12. A kit comprising:
    (a) an endovascular prosthesis comprising a delivery device attachment portion;
    (b) the endovascular prosthesis delivery device defined in claim 1, and
    (c) a sheath element encasing the endovascular prosthesis and the endovascular prosthesis delivery device,
    wherein the delivery device attachment portion of the endovascular prosthesis is coupled to the pull wire of the endovascular prosthesis delivery device.

13. The kit defined in claim 12, further comprising a microcathether for receiving the endovascular prosthesis and the endovascular prosthesis delivery device.

14. An endovascular prosthesis delivery device comprising:
    a tubular member having a distal portion and a proximal portion, the tubular member comprising a first lumen configured to receive a guidewire and a second lumen configured to receive a pull wire, the distal portion of the tubular member comprising a prosthesis attachment zone;

a hub insert element in a telescoping relationship with respect to the tubular member;

a pull wire disposed in the second lumen for attachment to a prosthesis; and a first retention element configured to secure at least a portion of the hub insert element and at least a portion of the tubular member with respect to one another;

wherein the first retention element is configured to: (i) secure the hub insert element with respect to the tubular member during delivery of the prosthesis, and (ii) be breakable to allow for relative movement of the hub insert element and the tubular member to release the prosthesis from the pull wire.

15. The endovascular prosthesis delivery device defined in claim 14, wherein the pull wire further comprises a pull wire sleeve in which the pull wire is disposed.

16. The endovascular prosthesis delivery device defined in claim 15, wherein the pull wire sleeve has a distal end disposed proximally with respect to the prosthesis attachment zone.

17. The endovascular prosthesis delivery device defined in claim 15, wherein the pull wire sleeve has a proximal end disposed distally with respect to the hub insert element.

18. The endovascular prosthesis delivery device defined in claim 15, wherein the pull wire sleeve has a proximal end disposed distally with respect to a proximal portion of the tubular member.

19. The endovascular prosthesis delivery device defined in claim 15, wherein the pull wire sleeve has an inner surface comprising a polymer lining.

20. The endovascular prosthesis delivery device defined in claim 15, wherein the pull wire sleeve has an inner surface comprising a polymer lining have a low coefficient of friction with respect to the pull wire.

\* \* \* \* \*